United States Patent
Volkl et al.

(10) Patent No.: US 10,441,391 B2
(45) Date of Patent: Oct. 15, 2019

(54) METHOD TO MANUFACTURE A COLORED BLANK, AND BLANK

(71) Applicant: DENTSPLY SIRONA Inc., York, PA (US)

(72) Inventors: Lothar Volkl, Goldbach (DE); Stefan Fecher, Johannesberg (DE); Martin Kutzner, Neuberg (DE); Tanja Oefner, Linsengericht (DE)

(73) Assignee: DENTSPLY SIRONA Inc., York, PA (US)

( * ) Notice: Subject to any disclaimer, the term of this patent is extended or adjusted under 35 U.S.C. 154(b) by 42 days.

(21) Appl. No.: 15/464,316

(22) Filed: Mar. 20, 2017

(65) Prior Publication Data
US 2017/0273764 A1    Sep. 28, 2017

(30) Foreign Application Priority Data

Mar. 23, 2016  (DE) .................. 10 2016 105 482
Apr. 7, 2016    (DE) .................. 10 2016 106 370

(51) Int. Cl.
*A61C 13/083*    (2006.01)
*A61C 13/00*     (2006.01)
(Continued)

(52) U.S. Cl.
CPC ........ *A61C 13/0022* (2013.01); *A61C 13/082* (2013.01); *A61C 13/083* (2013.01);
(Continued)

(58) Field of Classification Search
None
See application file for complete search history.

(56) References Cited

U.S. PATENT DOCUMENTS

| 4,818,626 A | * | 4/1989 | Werdecker | ............ C04B 35/581 427/123 |
| 5,480,532 A | * | 1/1996 | Schlott | .................... C04B 35/01 204/192.29 |

(Continued)

FOREIGN PATENT DOCUMENTS

| DE | 102011055393 A1 | 5/2013 |
| EP | 2965713 A1 | 1/2016 |

(Continued)

OTHER PUBLICATIONS

International Search Report; PCT/US2014/068317; Feb. 3, 2015 (completed); dated Feb. 11, 2015.

(Continued)

*Primary Examiner* — Peter A Salamon
(74) *Attorney, Agent, or Firm* — Dentsply Sirona Inc.

(57) ABSTRACT

The invention relates to a method for manufacturing a colored blank, which contains zirconium dioxide and is intended for the manufacture of a dental restoration, whereby raw materials in powder form, at least some of which contain one coloring substance each, are mixed with, zirconium dioxide as the main ingredient, the resulting mixture is pressed and subsequently subjected to at least one thermal treatment. To generate the desired fluorescence, it is intended that in the raw materials in powder form one uses as coloring substances at least terbium, erbium, cobalt, as well as one substance that generates a fluorescence effect in the dental restoration, however not iron, aside from naturally occurring impurities.

48 Claims, 12 Drawing Sheets

(51) Int. Cl.
*A61C 13/08* (2006.01)
*A61K 6/00* (2006.01)
*A61K 6/02* (2006.01)
*A61K 6/04* (2006.01)
*C04B 35/48* (2006.01)
*A61C 13/09* (2006.01)

(52) U.S. Cl.
CPC ............ *A61C 13/09* (2013.01); *A61K 6/0002* (2013.01); *A61K 6/0094* (2013.01); *A61K 6/024* (2013.01); *A61K 6/025* (2013.01); *A61K 6/0255* (2013.01); *A61K 6/04* (2013.01); *C04B 35/48* (2013.01); *C04B 2235/3244* (2013.01); *C04B 2235/40* (2013.01)

(56) References Cited

U.S. PATENT DOCUMENTS

| | | | | |
|---|---|---|---|---|
| 5,531,948 | A * | 7/1996 | Schlott | C04B 35/457 204/298.13 |
| 5,660,599 | A * | 8/1997 | Schlott | C04B 35/457 204/192.1 |
| 6,187,253 | B1 * | 2/2001 | Schlott | C04B 35/457 204/298.13 |
| 8,541,329 | B2 | 9/2013 | Ritzberger | |
| 2004/0072121 | A1 * | 4/2004 | Filser | A61C 13/0003 433/25 |
| 2004/0151367 | A1 * | 8/2004 | Wolf | A61C 13/0004 382/154 |
| 2004/0158342 | A1 * | 8/2004 | Wolf | A61C 13/0004 700/98 |
| 2005/0100856 | A1 * | 5/2005 | Filser | A61C 13/0003 433/49 |
| 2005/0146064 | A1 * | 7/2005 | Fecher | A61C 13/0004 264/19 |
| 2007/0046663 | A1 * | 3/2007 | Brinkmann | G01B 11/2522 345/419 |
| 2007/0072151 | A1 * | 3/2007 | Volkl | A61C 13/34 433/213 |
| 2007/0108645 | A1 * | 5/2007 | Von Schroeter | A61C 13/0003 264/16 |
| 2010/0015570 | A1 * | 1/2010 | Kutzner | A61C 13/0006 433/167 |
| 2010/0062396 | A1 * | 3/2010 | Hock | A61C 8/0012 433/201.1 |
| 2012/0012789 | A1 * | 1/2012 | Yamada | A61C 13/083 252/301.6 R |
| 2012/0114516 | A1 * | 5/2012 | Hachenberg | A61C 13/0022 419/25 |
| 2012/0175801 | A1 | 7/2012 | Jahns | |
| 2012/0214134 | A1 | 8/2012 | Khan | |
| 2015/0010880 | A1 * | 1/2015 | Fecher | A61C 9/002 433/50 |
| 2015/0173869 | A1 | 6/2015 | Jung | |
| 2015/0282905 | A1 | 10/2015 | Jahns | |
| 2017/0020639 | A1 * | 1/2017 | Jahns | A61C 8/0012 |
| 2017/0273764 | A1 * | 9/2017 | Volkl | A61C 13/0022 |

FOREIGN PATENT DOCUMENTS

| | | | |
|---|---|---|---|
| EP | 3108849 | A1 | 12/2016 |
| FR | 2781366 | A1 | 1/2000 |
| WO | 9947065 | A1 | 9/1999 |
| WO | 2005070322 | A1 | 8/2005 |
| WO | 2013055432 | A1 | 4/2013 |
| WO | 2013094669 | A1 | 6/2013 |
| WO | 2014164199 | A1 | 10/2014 |
| WO | 2015084931 | A1 | 6/2015 |
| WO | WO-2015084931 | A1 * | 6/2015 ........... A61C 8/0012 |
| WO | 2015199018 | A1 | 12/2015 |
| WO | 2016019114 | A1 | 2/2016 |

OTHER PUBLICATIONS

International Preliminary Report on Patentability Chapter I; PCT/US2014/068317; Feb. 3, 2015 (completed); dated Feb. 11, 2015.
Written Opinion of the International Searching Authority; PCT/US2014/068317; Feb. 3, 2015 (completed); dated Feb. 11, 2015.
International Search Report; PCT/EP2017/056526; Sep. 6, 2017 (completed); dated Sep. 16, 2017.

* cited by examiner

METHOD TO MANUFACTURE A COLORED BLANK, AND BLANK

THE CROSS-REFERENCE TO RELATED APPLICATIONS

This patent application claims the benefit of and priority to German Patent Application No. 10 2016 106 370.3, filed on Apr. 7, 2016 and German Patent Application No. 10 2016 105 482.8, filed on Mar. 23, 2016, which are herein incorporated by reference for all purposes.

TECHNICAL FIELD

The invention relates to a method for producing a colored blank that contains zirconium dioxide and is intended for the production of a dental restoration, whereby raw materials in powder form, at least some of which contain coloring substances, are mixed and the resulting mixture is pressed and subsequently is subjected to a thermal treatment.

BACKGROUND

Because of its strength and stability, zirconium dioxide is widely used in the dental field, for example as framework material for crowns and bridges.

Described in WO 99/47065 A1 is a method for the manufacture of a dental prosthesis, which is based on a zirconium dioxide blank and is to be fitted onto a pre-prepared tooth stump. The blank consists of a pre-sintered zirconium dioxide disk, from which a shape is worked out that corresponds to that of the dental prosthesis, in particular allowing for the shrinkage characteristics during the final sintering stage. The starting powder can contain coloring elements, which are present in oxide form.

Known from WO 2005/070322 A1 is an inorganic/inorganic composite material and a method for the production thereof. In the production of the composite material, one subjects an oxide ceramic powder of $ZrO_2$ (zirconium oxide) to a shaping step and pre-sintering to create an open-pored crystalline oxide ceramic molded part, onto which one applies an infiltrating substance in vacuum at room temperature, and sinters the oxide ceramic to full density under regular air and ambient pressure to create the inorganic/inorganic composite material. These measures are meant to produce an improvement in esthetical appearance.

In order to be able to provide restorations of the desired coloring, one uses raw materials in powder form that contain various coloring elements in oxide form, to create a mixture with a raw material in powder form that consists of non-pigmented zirconium dioxide, i.e. white zirconium dioxide. The zirconium dioxide on principle will be an yttrium oxide stabilized zirconium dioxide powder.

The fact that the coloring elements are uniformly distributed though the mixture created from the raw materials in powder form creates the advantage that the mixture to be pressed has a homogeneous coloring, so that as a result during the subsequent machining of a pre-sintered or possibly even fully sintered blank it will be ensured that the produced dental restoration exhibits the same coloring all over its outside surface and throughout its body. Fundamentally different from this method is an alternative process for coloring a dental restoration. Here, the latter in its completed state is immersed into a coloring solution. Since the penetration of coloring ions decreases with increasing distance from the surface, i.e. one obtains a coloring gradient, one faces the drawback that in cases when a corresponding restoration has to be reworked, different regions may have differing color characteristics. This is equally true of the fluorescence characteristics of a corresponding restoration that contains bismuth ions as the substance generating the fluorescence, as is described in WO 2014/164199 A1.

Known from WO 2015/199018 A1 is a colored translucent zirconium dioxide body that consists of yttrium oxide stabilized zirconium dioxide, erbium oxide, iron oxide, cobalt oxide, or aluminum oxide.

The objective of the present invention is to further develop a method of the above-mentioned type so that the completed restoration not only possesses the desired color but also fluorescence characteristics that at least are close to that of a natural tooth.

SUMMARY OF THE INVENTION

To meet this objective, the invention primarily proposes that, as the raw materials in powder form one uses as coloring elements at least terbium, erbium, cobalt, but no iron, aside from natural impurities, and that at least one of the raw material in powder form contains an element that generates a fluorescent effect in the dental restoration. In particular, it is intended that one of the raw materials in powder form contains—disregarding natural impurities—exclusively bismuth as the element generating the fluorescent effect, whereby a further raw material contains exclusively terbium or terbium and possibly praseodymium, another raw material in powder form contains only erbium, and a further raw material in powder form contains exclusively cobalt or cobalt and manganese and/or cerium.

The coloring elements and the element generating the fluorescence are preferably present in oxide from.

The corresponding raw materials in, powder form are on principle mixed with a further raw material in powder form to generate a mixture, which—apart from natural impurities—is, free of coloring elements and the element generating the fluorescent effect and consists of a powder of zirconium dioxide mixed crystal $Zr_{1-x}Me_xO_{2-(4n/2)_x}$, whereby Me represents a metal that is present in its oxide form and stabilizes the tetragonal or cubic phase of the zirconium dioxide. In the formula for zirconium dioxide mixed crystal, n=2, 3 or 4, and $0 \leq x \leq 1$.

In addition to the respective coloring element or element possessing the fluorescent properties, a corresponding zirconium dioxide mixed crystal powder is the main constituent of the other raw materials in powder form, whereby these on principle consist exclusively of the zirconium dioxide mixed crystal powder and the respective coloring element or elements or the element generating the fluorescent effect.

Exclusively zirconium dioxide mixed crystal powder in this context means that—as is customary—$HfO_2$, $Al_2O_3$ and other additives that are unavoidable for technical reasons may also be present.

In particular, the raw material, which is free of any coloring substances or of the element that generates the fluorescing effect, has the following composition in percent by weight:

$HfO_2 < 3.0$ $Al_2O_3 < 0.3$

Unavoidable impurities due to technical limitations $\leq 0.2$ (such as $SiO_2$, $Fe_2O_3$, $Na_2O$)

$Y_2O_3$ 4.5 to 9.5

$ZrO_2 = 100\% - (Y_2O_3 + Al_2O_3 + HfO_2 + $ unavoidable impurities$)$

In the following, this composition will be referred to as the zirconium dioxide base.

If an yttrium oxide stabilized zirconium dioxide is used to manufacture a dental prosthesis component with high strength and low translucency, then the yttrium oxide content should be between 4.5% by weight and 7.0% by weight, i.e. the uncolored zirconium dioxide powder used should possess the following composition in percent by weight.

$HfO_2 < 3.0$ $Al_2O_3 < 0.3$

Unavoidable impurities due to technical limitations ≤0.2 (such as $SiO_2$, $Fe_2O_3$, $Na_2O$)

$Y_2O_3$ 4.5 to 9.5

$ZrO_2 = 100\% - (Y_2O_3 + Al_2O_3 + HfO_2 + \text{unavoidable impurities})$

This composition hereinafter is referred to as zirconium dioxide variant I.

If an average strength and a higher translucency, relative to variant I, is required, then the yttrium oxide stabilized zirconium dioxide powder should have the following composition in percent by weight:

$HfO_2 < 3.0$ $Al_2O_3 < 0.3$

Unavoidable impurities due to technical limitations ≤0.2 (such as $SiO_2$, $Fe_2O_3$, $Na_2O$)

$Y_2O_3$ 7.0 to 9.5

$ZrO_2 = 100\% - (Y_2O_3 + Al_2O_3 + HfO_2 + \text{unavoidable impurities})$

The corresponding composition hereinafter will be referred to as variant II. In accordance with the invention, one creates from raw materials in powder form a mixture for a blank, which is homogeneously pre-colored and after complete sintering possesses fluorescence characteristics that correspond to those of a natural tooth. These advantageous features cannot be achieved in dental restorations, in which the fluorescence properties are obtained by immersion of a pre-sintered restoration into a solution that contains the corresponding ions.

The invention's teaching in particular offers the benefit that it becomes possible to produce a blank that possesses regions with differing fluorescence characteristics This becomes possible by filling into a mold at first a layer of a first mixture, created of raw materials in powder form, by filling then onto the first layer at least a second mixture, with a composition different from that of the first mixture, and by subsequently subjecting the mixtures together to pressing and a thermal treatment. Prior to introducing the second mixture, a first open cavity is formed in the layer consisting of the first mixture and then is filled with the second mixture, whereby it is not necessarily required that the second mixture is applied, onto the first mixture outside of the cavity.

It is also possible that after the second mixture has been introduced, a second open cavity is formed in it, in order to subsequently fill into the second open cavity a third mixture, which possesses a composition that is different from that of the first and/or second mixture.

As further development it is intended that in the layer consisting of the first mixture several first open cavities are created and that into these is filled a mixture of raw materials in powder form, in particular the second mixture.

In this, it is possible that at least a few or more open first cavities possess differing internal geometries.

In particular it may be intended that the raw materials in powder form used in the mixture contain—in addition to various coloring elements or constituent fractions thereof and/or differing constituent fractions of the element possessing the fluorescing characteristics—zirconium dioxide as main component, with a proportion of more than 80% by weight. Contained as further constituents can be yttrium oxide or calcium oxide or cerium oxide, but in particular yttrium oxide. The constituent fraction of yttrium oxide may vary in the mixtures of different compositions, in order to influence the strength of the, restorations to be manufactured from the blank.

In this, the mixture that will be used to form the dentine region of a restoration, for example of an artificial tooth, may contain a lower yttrium oxide content than the mixture that is used for the incisal region.

The layers also may have identical $Y_2O_3$ content but differing contents of coloring elements or of Bi.

In particular, the mixture intended for the dentine region should contain an yttrium oxide content between 4.5 and 7% by weight, relative to the sum of yttrium oxide and zirconium dioxide. The mixture for the incisal region should be chosen to possess an yttrium oxide content between 7.0% and 9.5% by weight, also relative to the sum of the yttrium oxide and the zirconium dioxide. As mentioned above, the content of yttrium oxide for the dentine region should always be lower than that for the incisal region.

The invention's teaching specifies that a blank is used to create a restoration that contains regions with differing colorations and/or fluorescence characteristics, and/or strength values and/or translucency characteristics, in order to be, able to realize properties like those of a natural tooth.

In a further development, areas in which one desires a reduced fluorescence, are covered by staining, so that one achieves the appearance that corresponds to the natural age of a tooth.

The invention is also characterized by a method for manufacturing a blank from a ceramic material, whereby at least two layers of ceramic material are filled layer by layer into a mold, whereby the ceramic materials consist of mixtures described above and whereby the layers may possess differing compositions, and subsequently, after the layers have been filled in, they are pressed and subsequently sintered, whereby after filling of the first layer its surface is being structured in such a way, that the first layer—viewed along its surface—has regions with differing heights, i.e. does not possess a uniform filling height, and that subsequently a second layer, which has a composition different from that of the first layer, is introduced into the mold.

An alternative option is that after introduction of the first layer, an intermediate layer of a ceramic material of a mixture according to the invention and different from the material of the first layer is filled into the mold onto the first layer, that the material of the first layer is mixed with the material of the intermediate layer, and that subsequently the second layer is introduced Into the mold. In this, it is particularly intended that the material of the intermediate layer is mixed with that of the first layer starting from the free surface of the intermediate layer over a height distance that corresponds to twice or approximately twice the height of the intermediate layer. Further it is particularly intended that the material of the intermediate layer be a material that is identical to that of the second layer.

According to the first alternative of the invention, one at first introduces a first layer of a bulk material into a mold.

This can for example be a tooth-colored zirconium dioxide granulate that has for example a bulk density between 1 $g/cm^3$ and 1.4 $g/cm^3$, in particular in the range between 1.15 $g/cm^3$ and 1.35 $g/cm^3$. After introduction of the granulate which may possesses a grain size D50 between 40 μm and 70 μm, the surface is smoothed out, in order to subsequently create a structure in a manner that results in elevations and valleys that in particular extend in parallel with respect to each other, in particular concentrically or parallel relative to each other. For this it is in particular intended that the structure is formed by an element that moves, in particular rotates relative to the first layer, and that in particular structures the surface region of the first layer by means of a section that is embodied with a wavy, comb-like, or serrated shape. This results in a quasi "raking" of the surface to form the surface pattern, i.e. the alternating elevations and valleys.

In particular it is intended that the structure is created in such a way that the volume of the elevations is equal or approximately equal to the volume of the depressions or valleys.

Preferably the serrated element possesses V-shaped teeth that are embodied symmetrically and possess side edges that enclose an angle between 15° and 45°. The spacing between consecutive teeth, i.e. the point-to-point distance should be between 1 and 4 mm, preferably between 1 mm and 3 mm.

Now one introduces into the mold the second ceramic bulk material, the quantity of which starts increasing starting in the depressions of the structure formed by the valleys, so that in consequence of this one achieves a quasi-continuous increase of the proportion of the second layer as one moves higher up the elevations. After the surface has been smoothed out, the layers are pressed, which results in a density in the region of around 3 $g/cm^3$.

This is followed by a pre-sintering at a temperature between 700° C. and 1100° C., in particular in the region between 800° C. and 1000° C., for a duration of for example 100 min to 150 min. The blank produced in this manner is subsequently machined, e.g. by milling and/or grinding, to produce a desired dental restoration, which is subsequently sintered until a final density is reached, which for example for zirconium dioxide is between 6.0 and 6.1 $g/cm^3$.

The sintering to final density can for example take place for a duration between 10 min and 250 min at a temperature between 1300° C. 1600° C. The sintering to final density can also be performed at a slight higher temperature. If the sintering takes place at a temperature that is for example 100° C. higher than the temperature for sintering to full density specified by the manufacturer of the raw material, then this is considered over-sintering, as long as the sintering time is the same as the time that applies for sintering to full density.

In particular, the sintering to final density takes place in a range between 1350° C. and 1550° C., whereby densities between 6.00 and 6.10 $g/cm^3$, in particular between 6.04 and 6.09 $g/cm^3$ can be achieved.

The above-specified temperatures and durations for the pre-sintering or sintering to final density or over-sintering apply to different layer shapes, layer sequences, and different numbers of layers, whereby this naturally also encompasses the manufacture of a blank that consists of one homogenous material, i.e. not of layers or areas of ceramic materials that possess differing compositions with respect to the raw materials.

The inter-penetrating layers offer the advantage that different physical and optical properties can be obtained throughout the height of the blank. For example, if the first layer has been colored to the, required degree, one obtains after the complete sintering a tooth-colored edge region, in which through the transition regions—created by the inter-penetrating first and second layer materials—the intensity of the tooth color decreases continuously and at the same time the translucency increases in the desired fashion. Subsequently the dental restoration is manufactured from the blank, in particular by milling that takes into account the layer positions, whereby the dental restoration is "positioned" inside the blank in such a way that the incisal extends within the region of the second layer.

Adding the oxide that generates the fluorescent effect, such as bismuth oxide, makes it possible to create a dental restoration with a visual appearance that is effectively indistinguishable from that of a natural tooth or a jaw region comprising several teeth.

Irrespective hereof, the invention's teaching ensures a continuous transition between the layers, so that color or translucency decrease or increase continuously, and it also becomes possible to implement modifications with respect to flexural strength in such a way that areas of the dental restoration that are subjected to special stresses will possess a greater flexural strength than areas subjected to lower stresses. This is accomplished without any abrupt changes, but as above-mentioned with a continuous, i.e. quasi constant transition, in particular over the height extent of the dental restoration to be manufactured, a technical possibility unknown in the state of the art, since either layers of different compositions are arranged one upon the other, which produces step-like changes, or the materials properties are modified exclusively from the exterior surface, i.e. throughout the entire dental restoration and not in dependence on its height.

In a preferred manner it is intended that the option of mixing the layer materials is realized by an element, which in particular is rotated about an axis that extends along the longitudinal axis of the mold, to create the structure, which may also be said to have a wave-like or serrated shape, by displacing material in the surface of the first layer. It is also possible to create the structure using a pressure element acting upon the surface of the first layer, whereby the pressure element in particular possesses elevations that surround depressions with both extending on the surface, so that the negative shape of the element, also referred to as stamper, is embossed into the surface of the first layer. Subsequently, as was explained above, the ceramic material of the second layer is filled in, smoothed out, and subsequently the layers are subjected to pressing whereupon the compacted part, is pre-sintered.

The invention is further characterized by that the first and the second layer, in their contacting, areas inter-penetrate each other over a height H, which has a magnitude of 1/15 to one quarter, in particular 1/10 to 1/5 of the total height of the first and second layer.

In its unstructured state, the first layer should have a height of approximately 1/2 to 2/3 of the sum height of the first and second layer.

In order for the first layer to be characterized by a high stability and the second layer to be translucent to the desired degree, the invention intends as a further development that the proportion of yttrium oxide in the first layer is 4.7 to 7.0% by weight and/or the proportion in the second layer is 7.0 to 9.5% by weight, whereby the proportional content of yttrium oxide in the first layer is lower than that in the second, layer.

In addition, the quotient of the tetragonal phase relative to the cubic phase of the zirconium dioxide after the pre-sintering should be ≥1 in both the first layer and the second layer.

In particular it is intended that the zirconium dioxide in the first layer be present to at least 95% in the tetragonal crystalline form. In the second layer the occurrence of the tetragonal crystalline phase should be between 51% and 80%. The remainder should be formed in particular by the cubic crystalline phase.

Consequently, the invention is characterized by the following not exhaustive list of measures. At first a tooth-colored, colored ceramic material consisting predominantly of zirconium dioxide, is filled into a mold. In this, the filling height corresponds to approximately ½ to ⅔ of the height of the blank prior to pressing.

Subsequently, the surface is patterned by a special structured element or a stamper, whereby the structure can be designed for a continuous transition of characteristics from the first material to the second material. Also possible is an alignment of the surface geometry of the first layer to the diffusion coefficients of the layer materials.

Preferably employed is a rotating element that is lowered, into the mold, i.e. into the mold containing the first layer and then is immersed into the first layer to the necessary degree. By rotating the element, which is structured on the side facing the layer, e.g. with a wave-like or comb-like shape, the surface is structured in a specific way. Alternatively, the surface can be structured by a stamper with a suitable geometry.

Subsequently, the mold is filled with the second, in particular less colored, ceramic material, which should possess a higher translucency and also a higher yttrium oxide content. This is then followed by a standard pressing of the ceramic materials and by pre-sintering.

The raw materials that are mixed to manufacture the layers contain elements that generate fluorescence characteristics, such as Bi, appropriate to the desired fluorescence characteristics.

It is also still within the scope of the invention if after introduction of the first layer, which preferably is colored to match a tooth color and consists predominantly of zirconium dioxide, another material is filled into the mold to form an intermediate layer. This material should be less colored than the first material but also consist predominantly of zirconium dioxide, which has an yttrium oxide content that is greater than that of the first layer. The intermediate layer can for example have a height of ⅒ to ⅕ of the total height of the layers to be introduced into the mold. Subsequently, the intermediate layer material is mixed with the first layer. In this, intermixing is performed by means of an element that penetrates into the first layer at least to a depth that corresponds to the height of the intermediate layer. Subsequently, one fills a layer in accordance with the second layer mentioned above into the mold, which will result in greater translucency and should contain a higher yttrium oxide content than the first layer. As explained above, this is followed by the pressing of the ceramic materials to form a blank and the pre-sintering, in order to subsequently work out a dental restoration from of the blank produced in this manner, in particular by milling or grinding. This is followed by a further processing step, the sintering to final density. The material of the intermediate layer should be that of the second layer.

Independently of the above-described methods, after the sintering to final density one obtains a monolithic dental restoration, without the need to apply veneering ceramic, even though it would still, be within the scope of the invention to do so.

A pre-sintered or fully sintered blank to be used in the manufacture of a dental restoration, such as a dental framework, crown, partial crown, bridge, coping, veneer, abutment, post and core, consisting of a ceramic material that in particular contains zirconium dioxide, which comprises along its height layers of different compositions, is characterized in that the blank comprises three layers, one of which, the middle layer, extends over at least ⅒ to ⅕ of the height of the blank and consists of a material of the first layer and a material of the second layer or of an intermediate layer material. The invention is in particular characterized in that in the middle layer the proportion of the material of the first layer decreases continuously or largely continuously from the first layer along the direction towards the second layer.

The invention creates the possibility of creating a continuous transition between the first layer and the second layer, so that as a consequence a continuous change of the coloring and translucency is possible even for colored layer materials. It becomes possible to attain any desired fluorescence characteristics. Provisions in this regard also offer the possibility of modifying strength properties to the desired degree, whereby in particular in those regions that are subject to high stresses, such as the lower side of bridge connectors, will be worked out of the region of the blank in which extends the first layer, which possesses the highest rigidity.

In particular it is intended that the ceramic material contains at least 85% by weight of zirconium dioxide, which is doped with yttrium oxide, whereby the yttrium oxide content in the first layer is as high as 7.0% by weight and the yttrium oxide content in the first layer is lower than in the second layer.

Further, as further development of the invention it is intended that the first layer is colored differently and/or has a different level of yttrium oxide doping than the second layer in such a way that the fully sintered restoration—viewed along the tooth axis—will have greater strength on the root side than on the incisal side and/or a higher translucency on the incisal side than on the root side.

A dental restoration, in particular a crown, partial crown, or bridge, manufactured from a blank of the above-described type is in particular characterized in that the restoration—viewed along the tooth axis—consists of at least a first layer extending on the root side, a second layer extending on the incisal side, and a middle layer, which extends in between these and which possesses a strength that decreases and/or a translucency that increases continuously or largely continuously from the first layer along the direction towards the second layer. This allows attaining any fluorescence that might be called for.

The invention's teaching makes it possible to manufacture a dental restoration in a cost-effective and reproducible manner, without any compelling need to manually apply a veneering ceramic to the incisal. One also has the possibility to adjust the strength by way of the composition of the ceramic materials, so that the highest flexural strength is attained in the region with the highest loads.

Further details, advantages, and features of the invention are not only found in the claims, the characteristic features mentioned therein, individually and/or in combination, but also in the following description of, preferred embodiment examples.

DETAILED DESCRIPTION OF THE INVENTION

Figure 1:
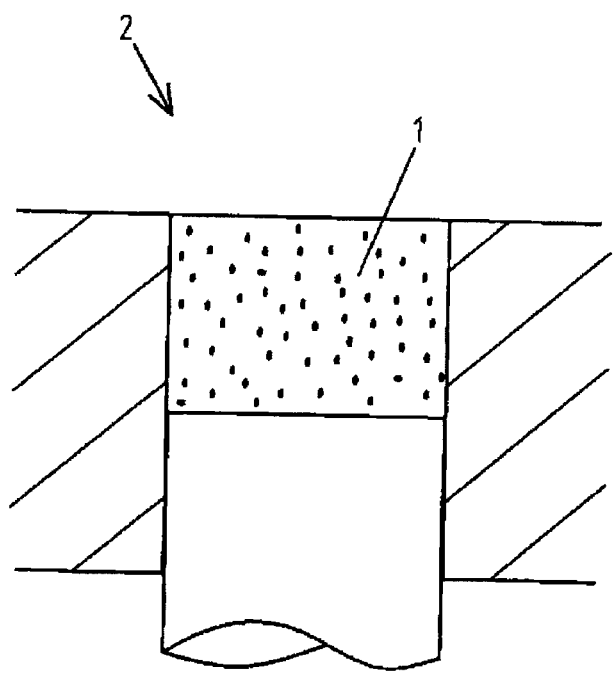
FIG. 1 shows a schematic diagram of a device for manufacturing a blank.

In the production of a dental restoration, one at first produces several starting raw material mixtures in powder form, which have the following composition:

Raw material 1 zirconium dioxide base (unpigmented zirconium dioxide powder) in percent by weight $HfO_2 < 3.0$ $Al_2O_3 < 0.3$ Unavoidable impurities due to technical limitations ≤0.2 (such as $SiO_2$, $Fe_2O_3$, $Na_2O$)

$Y_2O_3$ 4.5 to 9.5

$ZrO_2 = 100\% - (Y_2O_3 + Al_2O_3 + HfO_2 + \text{unavoidable impurities})$

Raw material 1 zirconium dioxide variant I (unpigmented zirconium dioxide powder) in % by weight:

$HfO_2 < 3.0$ $Al_2O_3 < 0.3$

Unavoidable impurities due to technical limitations ≤0.2 (such as $SiO_2$, $Fe_2O_3$, $Na_2O$)

$Y_2O_3$ 4.5 to 7.0

$ZrO_2 = 100\% - (Y_2O_3 + Al_2O_3 + HfO_2 + \text{unavoidable impurities})$

Raw material 1 zirconium dioxide variant II (unpigmented zirconium dioxide powder) in percent by weight:

$HfO_2 < 3.0$ $Al_2O_3 < 0.3$

Unavoidable impurities due to technical limitations ≤0.2 (such as $SiO_2$, $Fe_2O_3$, $Na_2O$)

$Y_2O_3$ 7.0 to 9.5

$ZrO_2 = 100\% - (Y_2O_3 + Al_2O_3 + HfO_2 + \text{unavoidable impurities})$

Raw material 2: zirconium dioxide variant II without $Y_2O_3$ and with erbium oxide ($Er_2O_3$) content of 9.2% by weight Raw material 3; zirconium dioxide base, variant I or variant II with cobalt oxide ($Co_3O_4$) content of 0.04% by weight Raw material 4; zirconium dioxide base, variant I or variant II with terbium oxide ($Tb_2O_3$) content of 2.0% by weight Raw material 5; zirconium dioxide base, variant I or variant II with bismuth oxide ($Bi_2O_3$) content of 0.3% by weight The above-specified number of raw materials in powder form should not be understood to be a limiting factor to the scope of protection of the invention.

To produce an artificial tooth of the VITA color A2, one mixes the following portions of the raw materials in powder form into, a mixture;

91.40% by weight of raw material 1 zirconium dioxide variant II 3.80% by weight of raw material 2

1.25% by weight of raw material 3 (with zirconium dioxide variant II)

3.50% by weight of raw material 4 (with zirconium dioxide variant II)

0.05% by weight of raw material 5 (with zirconium dioxide variant II)

Additionally a binding agent may be added, which however is not taken into consideration in the above-listed percentages by weight.

The mixture 1 created in this manner then is filled into a mold 2 and pressed.

After the compacted piece has been removed from the mold, it is subjected to pre-sintering at a temperature between 800° C. and 1000° C. for a duration between 100 min and 150 min. In this, a de-binding takes place prior to the pre-sintering. After the pre-sintering, the density of the blank produced in this manner is approximately 3 g/m³. The breaking strength of the pre-sintered blank is in the region between 10 MPa and 60 MPa.

Subsequently the blank is provided with a holder or is accommodated by such, so that subsequently it can be machined in a milling or grinding machine, in order to work out an artificial tooth from the blank, for example for a dental restoration. This is followed by a sintering to final density at a temperature between 1450° C. and 1550° C., in particular at 1500° C. for a duration of 1-5 hours, in particular for 2 hours. The tooth produced in this manner possesses the tooth color VITA color A2 and possesses a fluorescence that corresponds to that of a natural tooth.

To produce the VITA color A4, one uses the following raw materials:
79.16% by weight of raw material 1 zirconium dioxide variant II
5.54% by weight raw material 2
7.50% by weight raw material 3 (with zirconium dioxide variant II)
7.50% by weight of raw material 4 (with zirconium dioxide variant II)
0.30% by weight of raw material 5 (with zirconium dioxide variant II)

This is followed by thermal treatments and thermal treatment and processing steps, which were explained above. The completed natural tooth possessed the desired VITA color A4 with a fluorescence that corresponds to that of a natural tooth.

In a further experiment to produce a dental prosthesis in the VITA color A4 with a greater strength than the dental prosthesis described above, the following raw materials were mixed:
80.46% by weight of raw material 1 zirconium dioxide variant I
5.54% by weight of raw material 2
6.25% by weight of raw material 3 (with zirconium dioxide variant I)
7.50% by weight of raw material 4 (with zirconium dioxide variant I)
025% by weight of raw material 5 (with zirconium dioxide variant I)

Even after the thermal treatment and the machining—as described above—it was found that the tooth possessed the VITA color A4 with a fluorescence.

FIGS. 2 to 7, in which identical elements always carry the same reference labels, will be used to illustrate an aspect that characterizes the present invention, which specifies the manufacture of a dental restoration with a monolithic structure from a ceramic material.

For this purpose the invention specifies the production of a blank that comprises regions of ceramic material that possess differing compositions and consequently possess properties that make it possible to achieve the desired optical and mechanical characteristics suitable for the particular restoration to be manufactured, and as mentioned above create the possibility to use the monolithically created dental prostheses immediately after sintering to final density, without the need, for example, to manually apply and burn an incisal.

It is also possible—in a targeted and selective manner—to achieve the desired strength values in those regions that are subject to high loads. Also achievable are the desired optical, such, as the color, translucency, and fluorescence characteristics.

Figure 2:
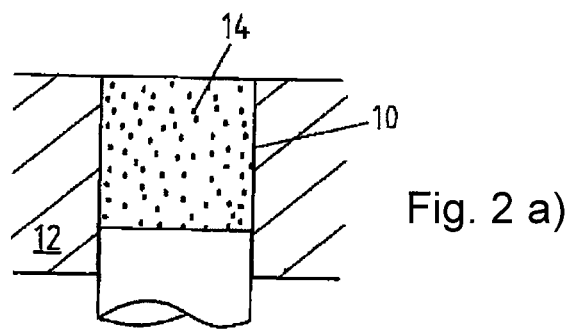
FIG. 2a) shows a schematic diagram of a device and a processing step performed with it, FIG. 2b) shows another schematic diagram of the device shown if FIG. 2a) and a processing step performed with it, FIG. 2c) shows another schematic diagram of the device shown in FIG. 2b) and a processing, step performed with it.
Figure 2:
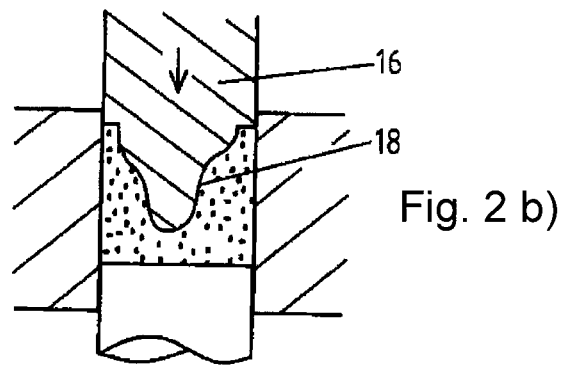
Figure 2:
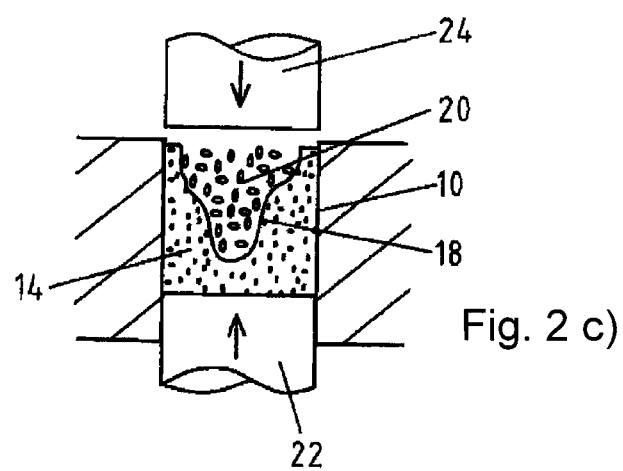
Figure 3:
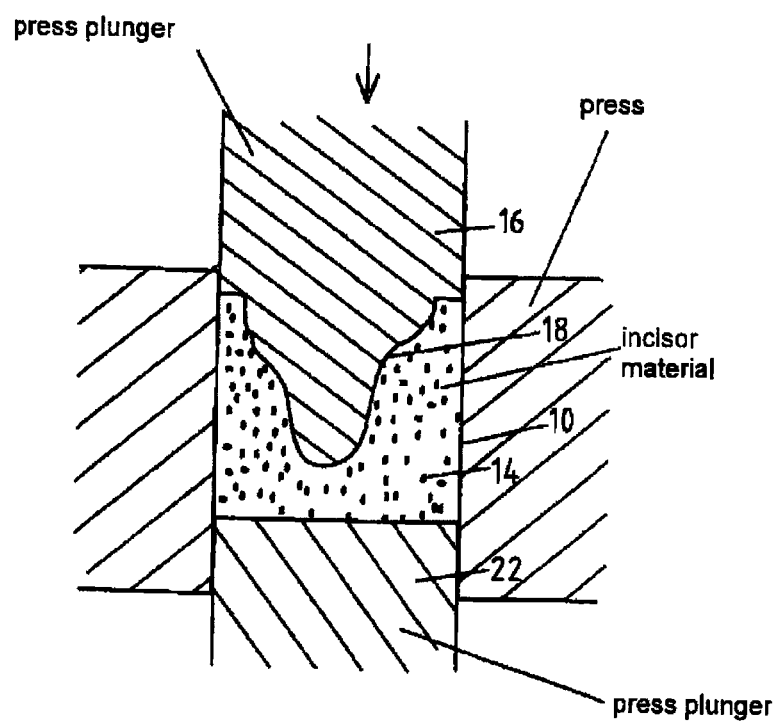
FIG. 3 shows an enlarged view of FIG. 2b)
Figure 4:
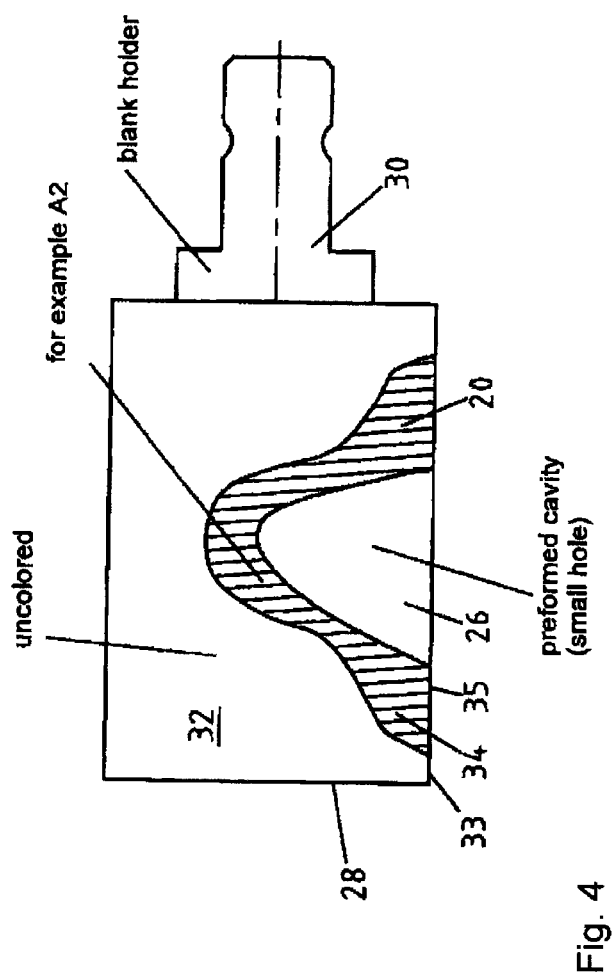
FIG. 4 shows a blank with regions of different material properties.

FIGS. 2 to 4 are used to describe the manufacture of a blank, from which a dental restoration can be produced, in particular a tooth in the embodiment example.

At first one fills powder of the first raw material variant II into a mold 10 since this material is meant to be used as incisal material. The corresponding powder may contain a binding agent.

The relatively high yttrium oxide content ensures that in the completed molded part, i.e. the dental restoration, the tetragonal crystal phase content is as low as 50 to 60%, whereby the rest is present in, the cubic and monoclinic crystal phases.

Subsequently an open cavity 18 is formed by means of a press stamper 16 in the material 14 or rather in the layer formed by this material. The material 14 is displaced or slightly compacted by means of the press stamper. After the cavity 18 has been formed (FIG. 2b), the press stamper 16 is removed and a second ceramic material 20, which may possess the following composition is filled into the cavity 18, to manufacture a dental prosthesis with the color VITA color A2:
91.66% by weight raw material 1 zirconium dioxide variant I
3.26% by weight raw material 2
2.0% by weight raw material 3 (with zirconium dioxide variant I)
3.0% by weight raw material 4 (with zirconium dioxide variant I)
0.08% by weight raw material 5 (with zirconium dioxide variant I)

Additionally, a binding agent may be present, but is not taken into consideration in the above-listed by-weight percentages.

In this, coloring oxides and bismuth oxide are present in such a quantity that one obtains the desired tooth color and fluorescence, since the second ceramic material 20 is used to form the dentine of the tooth to be manufactured.

Furthermore, the comparatively low proportion of $Y_2O_3$ ensures that the fully sintered dental prosthesis possesses a high tetragonal phase content of at least 85%, preferably at least 90%, which results in high stability.

After filling the second ceramic material 20 into the cavity 18 (FIG. 2c), the materials 14, 20, or rather the layers or regions formed from these materials, are then pressed in the mold 10 of the press 12—in particular by means of a lower or upper stamper 22, 24—, which is used for the compressing. After pressing, the density of the blank 28 is approximately 3 g/cm³ auf. Pressing preferably takes place at a pressure between 1000 bar and 2000 bar.

With respect to the materials 14, 20 it should be noted that their bulk density should be between 1 g/cm³ and 1.4 g/cm³. After pressing, the density is approximately 3 g/cm³.

FIG. 3 reproduces in more detail the illustration of FIG. 2b). It is evident that a cavity 18 has been formed by the press stamper 16 in the first ceramic material 14 or rather in the layer consisting of this material. On the bottom side, the mold 10 is bordered by the press stamper 22.

As is illustrated in FIG. 4, a second cavity 26 can be created in the second material 20 after its compression by means of the press stamper 22, 24 or possibly after the pre-sintering, e.g. by means of milling.

However, one also has the option to form a second cavity 26 in the material 20 of FIG. 2c), which completely fills the cavity 18 that is open on its bottom side, by means of a not illustrated press stamper.

Irrespective of whether the second cavity 26 is present or not, the blank 28 is pre-sintered after pressing, at a temperature in particular in the range between 800° C. and 1000° C. for a duration of between 100 min and 150 min. In this, a de-binding is followed by the pre-sintering. The density of the blank 28 after pre-sintering is approximately 3 g/cm³. The breaking strength of the pre-sintered blank 28 should be between 10 MPa and 60 MPa.

The blank 28 is then, equipped with a holder 30, so that subsequently the blank 28 can be machined, e.g. in a milling or grinding machine, to produce a dental restoration such as a tooth out of the blank 28, as will be explained with the help of FIG. 6. In this, the tooth to be produced is at least virtually placed inside the blank 28 in such a manner that the incisal region extends within the region 32 consisting of the first ceramic material 14 and the dentine region in parts extends in the second region 34 consisting of the second ceramic material 20. The subsequent machining of the blank 28 takes these data into consideration.

Figure 5:
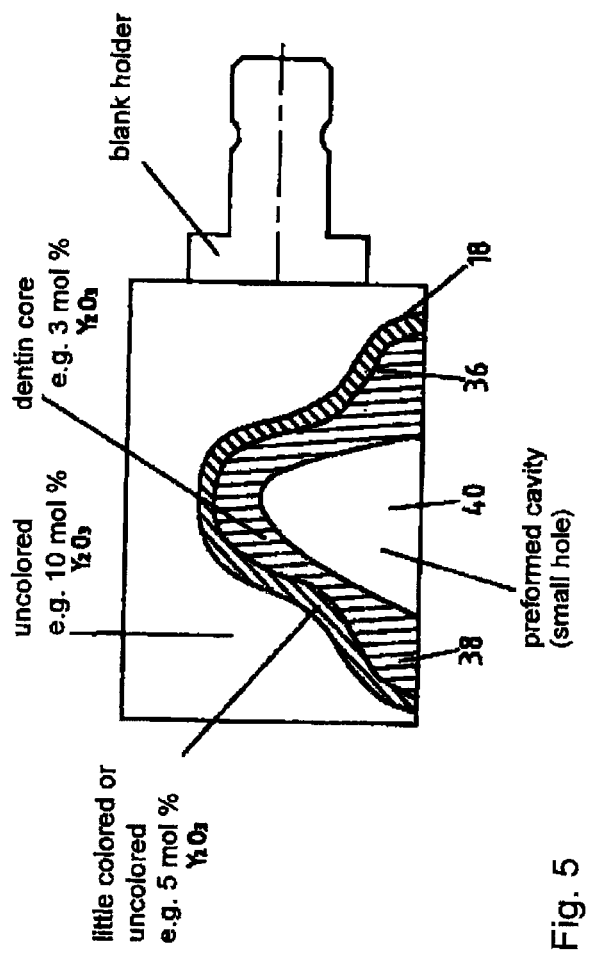
FIG. 5 shows a further blank, with regions of differing material properties.

FIG. 5 illustrates that after completing the first cavity 18 in the first ceramic material 14 and filling the second ceramic material 20 into the cavity 18, a second cavity 36 may possibly be created in accordance with the procedure according to FIG. 2b), in order to subsequently introduce into the cavity 36 formed in this manner a third ceramic, material 38, which differs in its composition from the second ceramic material in a way that in particular allows achieving a higher strength. As was explained in connection with FIG. 4 it is also possible to form a cavity 40 in the third ceramic material 38.

Figure 6:
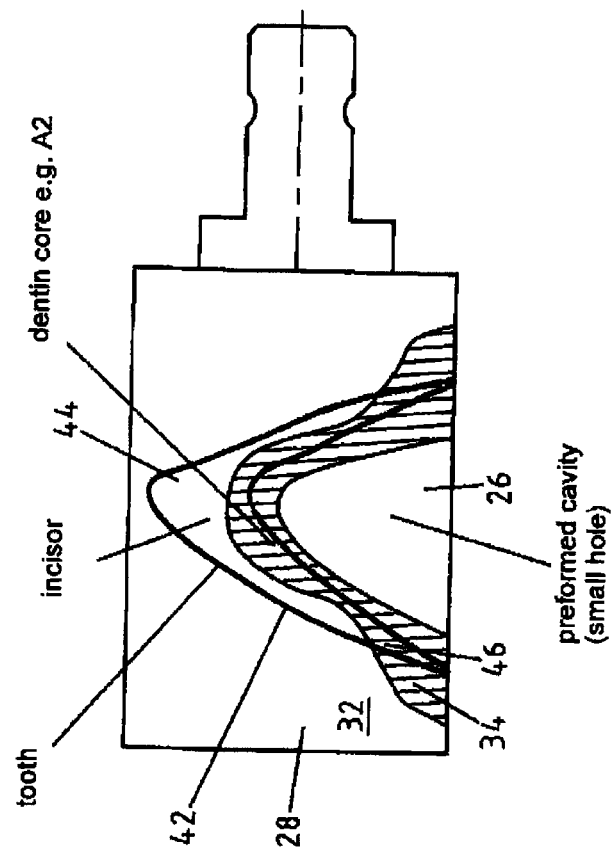
FIG. 6 shows a schematic diagram of a blank with the tooth to be produced from it.
Figure 7:
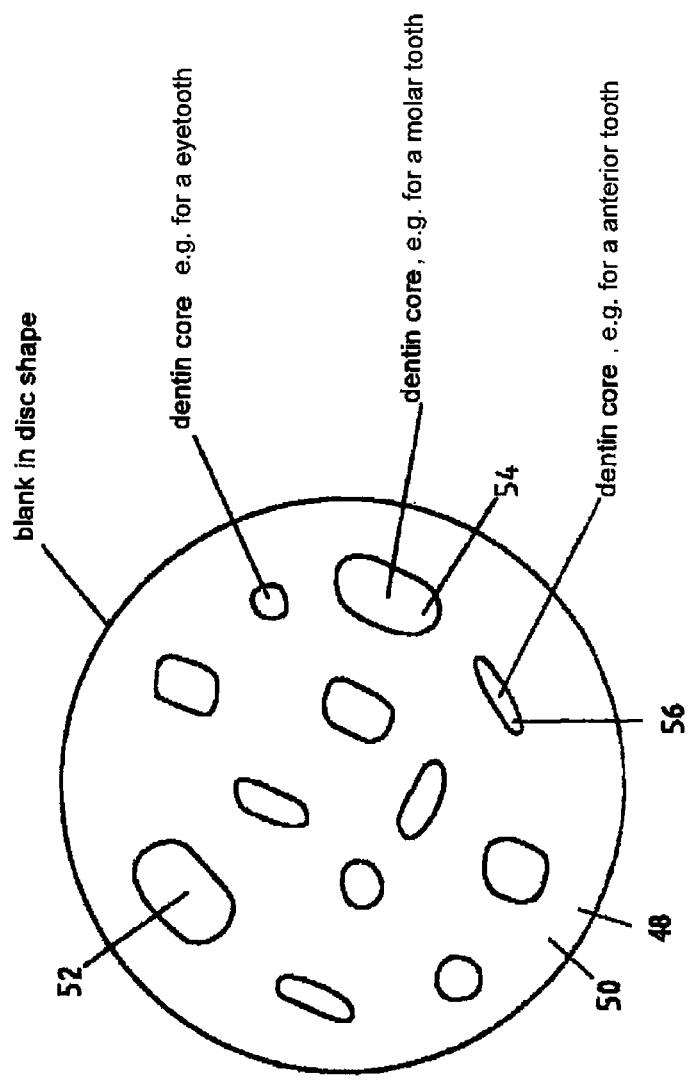
FIG. 7 shows a top view onto a blank with several regions of different material characteristics.

FIG. 6 illustrates how a dental restoration, a tooth 42 in the present embodiment example, is created out of the blank 28. For this purpose, knowing the extent of the first region 32 consisting of the first ceramic material 14 and the second region 34 consisting of the second ceramic material 20, the tooth 42 to be manufactured is virtually positioned inside the blank 28 into the regions 32, 34 in such a way that the incisal extends within the first region 32 and the dentine 46 extends within the second region 34.

After working the virtually positioned tooth 42 out of the blank 28, one has available a dental prosthesis that in principle can be deployed immediately, and in particular does not require any veneering. A monolithic tooth 42 is manufactured on the basis of the invention's teaching. In this, working the result out of the blank 28 is facilitated by the fact that the second region 34 already possesses an open cavity 26, as was explained in connection with FIG. 4 and is evident in FIG. 6.

The invention's teaching provides the possibility to create a blank 48 with a multitude of regions 52, 54, 56, that consist of the second and possibly of the third ceramic material and may possess different geometries (FIG. 7), to be able to produce teeth of different geometries. The so-called second regions 50, 52, 54, which are formed of the second ceramic material 20, are embedded in the first ceramic material 48, i.e. are surrounded by the latter, as is evident in the figures. The second regions 50, 52, 54 are not covered on the bottom side.

As is particularly well illustrated in FIGS. 3-5, the second regions exhibit exterior geometries that narrow with increasing distance from the bottom region, i.e, the base region 35. This can be referred to as a cone-like geometry, whereby the external contour is a freeform surface.

The base region 35, or rather the base surface bordering this region at the lower side, merges evenly into the lower side or bottom surface 33 of the first region 32.

To produce the sections 52, 54, 56 of the blank, which are also referred to as nests, one requires—as is explained in connection with FIG. 2—corresponding open cavities in the layer that is produced from the first material 14 and referred to as first region 50, in order to subsequently fill the cavities with the second ceramic material 20 in bulk form and to subsequently press, i.e. compact, the materials 14, 20 together.

It should be noted with respect to the physical characteristics of the materials 14, 20, that in addition to a different fluorescence, translucency, and rigidity characteristics, the two materials should also possess different thermal expansion coefficients. It is in particular intended by the invention that the first ceramic material 14 possesses after the sintering to full density a thermal expansion coefficient that is 0.2 μm/m*k to 0.8 μm/m*K lower than that of the second region 38, 52, 54, 56 that is formed by the second ceramic material 20. This generates a compressive stress in the first, region 50, i.e. in the incisal material, which results in an increase of the strength.

With respect to the blanks 28, 48 it should be noted that they may for example possess a cuboid shape with for example the dimensions 18×15×25 mm or a disk shape, e.g. with a diameter of 100 mm, without this placing any restrictions on the invention's teaching. This in particular offers the advantage—as is illustrated in connection with FIG. 7—that for example in a disk-shaped blank several second regions 52, 54. 56—so-called dentine cores—can be introduced to produce restorations of different geometries, but with a layer layout that is favorable with respect to translucency and rigidity.

Since the positions of one or several second regions 52, 56, i.e. of the nests, which possibly possess differing geometries, are known, they can be saved as records in a data set. Subsequently, the restorations to be manufactured are positioned relative to and within the sections of the blank, in order to create the dental prosthesis from the blank by milling and/or grinding.

In this, the artificial tooth to be manufactured is worked out of the blank 28, 48 in a way that takes into account the fluorescence characteristics generated during the sintering to full density, so that after the dense-sintering one, has available a tooth that is immediately useable.

Of course it is still within the scope of the invention's teaching if the artificial tooth is machined out of the blank only after the blank's sintering to full density.

A further embodiment of the invention's teaching is illustrated in FIGS. 8 to 12, where again identical elements carry the same reference labels. These figures also illustrate that the dental restorations can, be manufactured from a ceramic material and possess a monolithic structure of a nature so that after the sintering to final density a dental prosthesis is available for immediate use. For this it is intended according to the invention that a blank is manufactured that contains, several layers, which consist, of ceramic material but have differing compositions, which make it possible to achieve the particular optical and mechanical properties that are desired for a particular dental restoration to be manufactured, and that result in an immediate possible use of the dental prosthesis, without the need, for example, to manually apply and fire an incisal after the sintering to full density. It is also possible to obtain specific desired strength values in the regions that are subject to high loads, such as the lower sides of bridge connectors.

Figure 8:
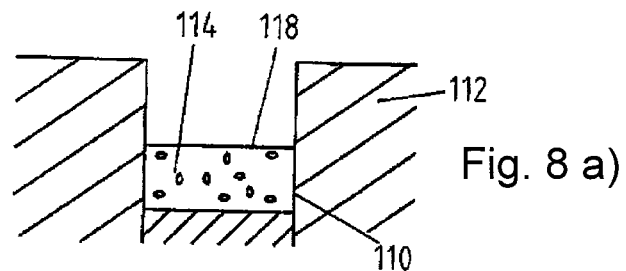
FIG. 8a) shows a schematic diagram of a device and a processing step it performs, FIG. 8b) shows a schematic diagram of the device shown in FIG. 8a) and another processing step it performs, FIG. 8c) shows a schematic diagram of the device shown in FIG. 8b) and another processing step it performs, FIG. 8d) shows a schematic diagram of the device shown in FIG. 8c) and another processing step it performs.
Figure 8:
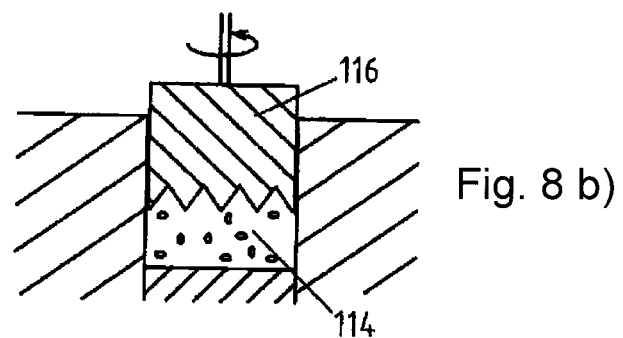
Figure 8:
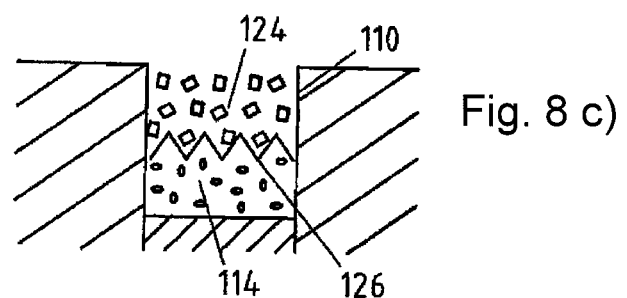
Figure 8:
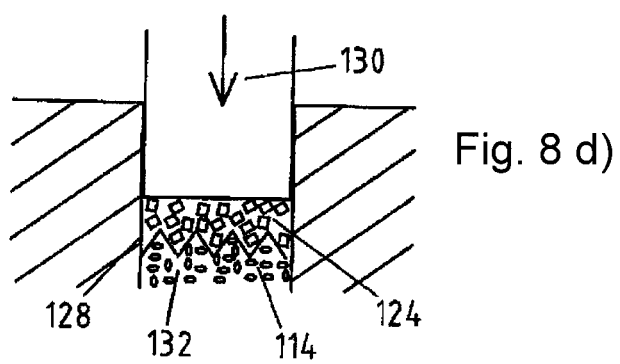
Figure 9:
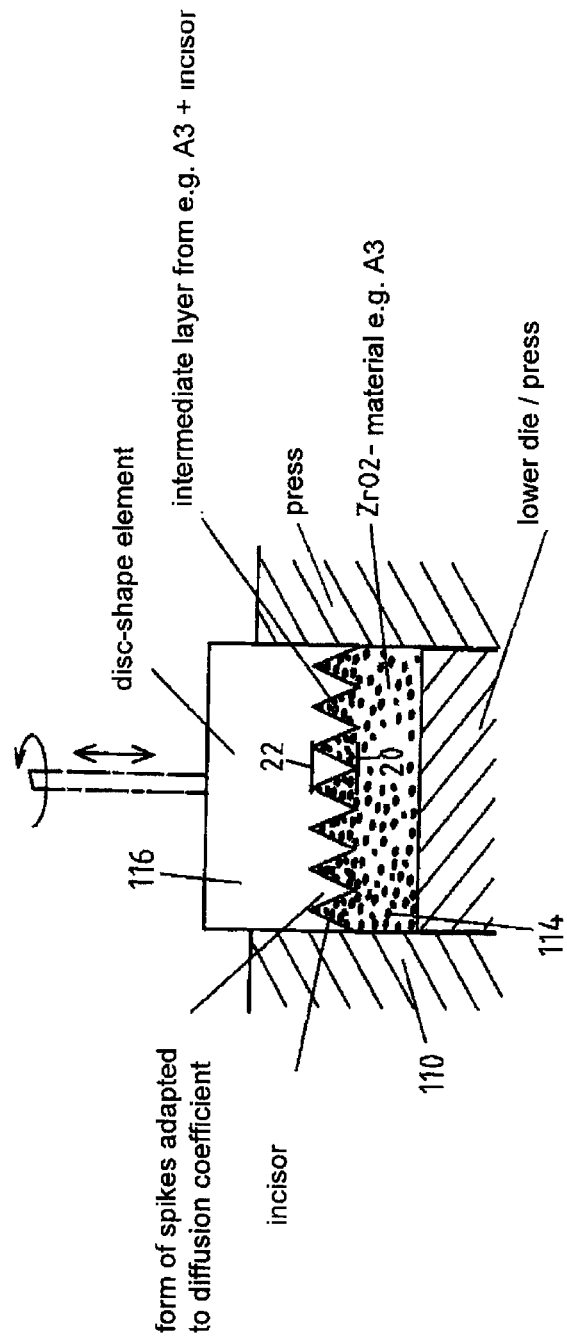
FIG. 9 shows an enlarged view of FIG. 8b), FIG. 10a) shows a schematic diagram to illustrate a characteristic of the blank, FIG. 10b) shows another schematic diagram to illustrate another characteristic of the blank, FIG. 10c) shows another schematic diagram to illustrate another characteristic of the blank, FIG. 10d) shows another schematic diagram to illustrate another characteristic of the blank.

FIGS. 8 and 9 illustrate the manufacture of a blank, from which a corresponding dental restoration can be produced. In accordance with FIG. 8a), into the mold 110 of a press 112 is at first filled a first material 114, which is a mixture, of raw materials in powder form of the above-described type with the following proportions:

97.19% by weight raw material 1 zirconium dioxide variant I 0.54% by weight raw material 2

1.25% by weight raw material 3 (with zirconium dioxide variant I)

1.00% by weight raw material 4 (with zirconium dioxide variant I)

0.01% by weight raw material 5 (with zirconium dioxide variant I)

Now the smoothed surface of the first layer 114 is provided with a pattern in accordance with step b). For this, one uses for example an element 116 with a disk- or plate- or bar-shaped geometry, which in the present embodiment example on the layer side possesses a serrated geometry, so that in the surface 118 of the layer 114 a corresponding negative pattern is formed by displacement of material. This structure is present as concentric elevations and valleys in between them. In this, the spacing between elevation (peak) and valley (depression), i.e. the clear distance between the projection 120 and the valley bottom 122 of FIG. 9 should be approximately ⅕ of the height of all layers.

In particular it is intended that the structure is applied in such a way that the volume of the elevations is equal or approximately equal to the volume of the depressions or valleys.

Subsequently the second layer 124 is filled into the mold 110 (FIG. 8c). The second layer 124 consists of a mixture of the raw materials in powder form with the following composition:

80.46% by weight; raw material 1 zirconium dioxide variant II 5.54% by weight: raw material 2

6.25% by weight raw material 3 (with zirconium dioxide variant II)

7.50% by weight raw material 4 (with zirconium dioxide variant II)

0.25% by weight raw material 5 (with zirconium dioxide variant II)

The overall height of the layers 114 and 124 is equal to twice the height of the layer 114 in its unstructured state, without this having any limiting effect on the scope of the invention's teaching.

While the first layer 114 preferably has a height that corresponds to half the overall surface H of the first and the second layers 114, 124, the height of the first layer 114 may also range between ½ H and ⅔ H and consequently that of the second layer 124 between ⅓ H and ½ H.

The fact that the material of the second layer 124 penetrates to the bottom of the valleys 126 in the surface 118 of the layer 114 results in a continuous transition between the properties of the layer 114 and the layer 124, after the layers 124, 114 have been pressed in accordance with FIG. 8d). The transition or intermediate layer is, identified with the reference label 128 in FIG. 8d).

The layer 124 consists of a material that is different from that of the layer 114. Differences exist in particular in the coloring agents, the element generating fluorescence, and the yttrium oxide content. The latter is chosen so that the proportion of the cubic crystalline phase in the layer 124 after pre-sintering is significantly higher than the one in the layer 114. In the layer 114, the fraction of the tetragonal crystal phase is greater than 90%, whereas the cubic crystal phase content in the layer 124 is between 30% and 49%. The rest essentially is present in the, tetragonal crystal phase.

These differences in the crystalline phase fractions are the result of an yttrium oxide content of between 4.5% and 7% by weight in the layer 114 and of 7% to 9.5% by weight in the layer 124, whereby the content in the first layer 114 is lower than the one in the second layer 124.

Irrespective of the different proportions of the raw materials in the layers 114, 124, a continuous color transition is realized between the layers 114 and 124. The higher yttrium oxide content reduces the flexural strength. One also obtains a higher translucency in the layer 124 in comparison to the layer 114.

Because of the higher bismuth oxide content in the layer 114 in comparison to the layer 124 one obtains desired fluorescence characteristics in the completed, dental reconstruction.

Figure 11:
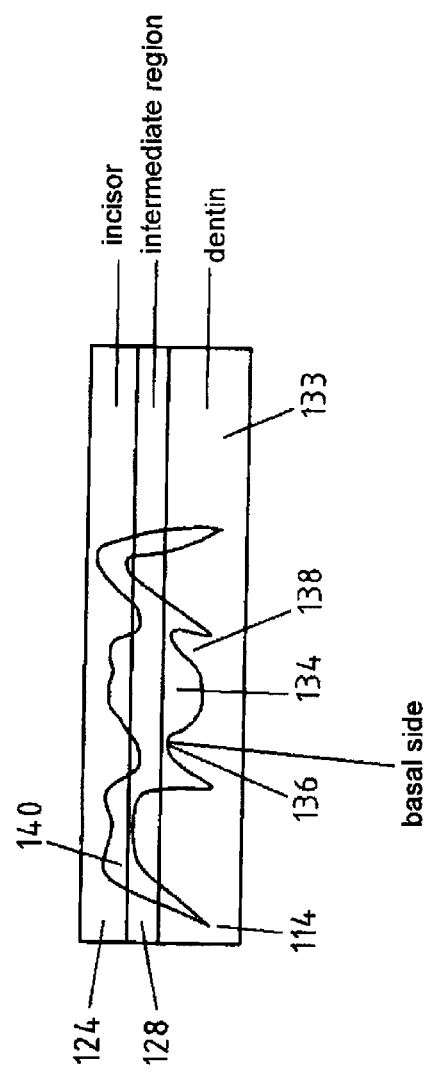
FIG. 11 shows a schematic diagram of a bridge to be produced from a blank of FIGS. 8a)-d), and FIG. 12a) shows a schematic diagram of an alternative method and a processing step performed with it, FIG. 12b) shows a schematic diagram of an alternative method and a processing step performed with it, FIG. 12c) shows a schematic diagram of an alternative method and a processing step performed with it, and FIG. 12d) shows a schematic diagram of an alternative method and a processing step performed with it.

The highest strength is found in the layer 114, which in the dental prosthesis to be created from the blank contains the regions that are subject to the highest loads, e.g. in particular the lower sides of the connectors of bridges, as is illustrated in FIG. 11.

The layers 114, 124 are pressed by means of a stamper 128, whereby the pressing takes place at a pressure of between 1000 bar and 2000 bar.

The material in bulk form, i.e. in the state in which it is introduced into the mold 110, has a bulk density between 1 g/cm$^3$ and 1.4 g/cm$^3$. The density after the pressing is approximately 3 g/cm$^3$.

As a result of the structuring, one finds in the transition region between the unmixed regions of the first and the second, layers 114 and 124, before the layers 114 and 124 have been compacted, a density that can be as high as 2 g/cm$^3$. The transition region may also be referred to as middle layer 128.

After pressing, the produced blank 133 is discharged from the mold 110 and is pre-sintered in the customary manner, in particular at a temperature between 800® C. and 1.000° C. for a duration between 100 min and 150 min. A corresponding blank is illustrated in FIG. 11. The blank 133 comprises the compacted layer 114, the compacted layer 124 and the compacted middle layer 128, i.e. the transition region.

If a dental prosthesis—in the embodiment example a bridge 134—is milled from the blank 133, the milling program should be designed so that the lower region of the bridge 134, in particular the area of the lower sides of the connectors 136, should be the location of the layer 114 with the greatest flexural strength. On the other hand, the incisal area 140 of the bridge is positioned within the layer 124.

In the transition area, i.e. in the middle layer 128, location of the quasi-continuous or continuous transition between the layers 114 and 124, is also the location of the transition between dentine and incisal. The dentine extends within the region 114.

Figure 10:
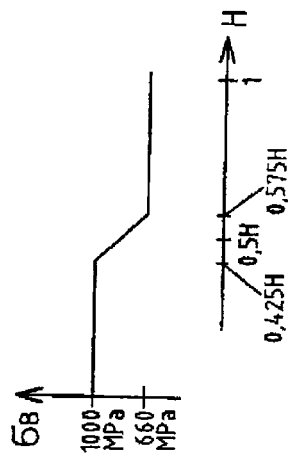
Figure 10:
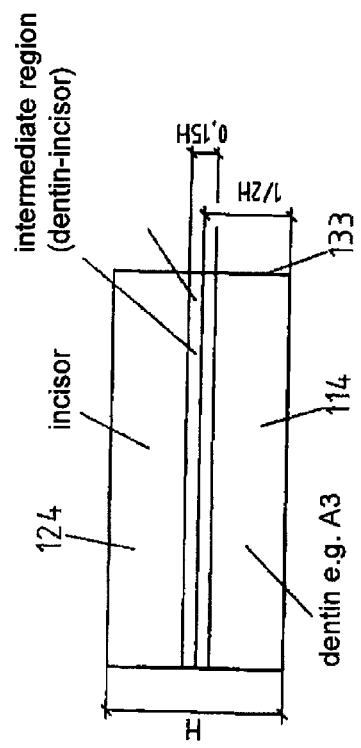
Figure 10:
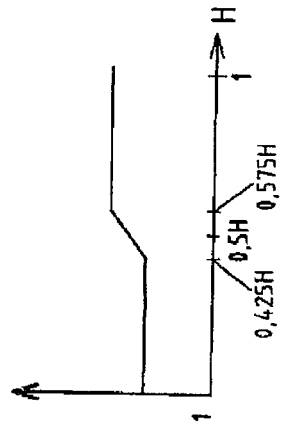
Figure 10:
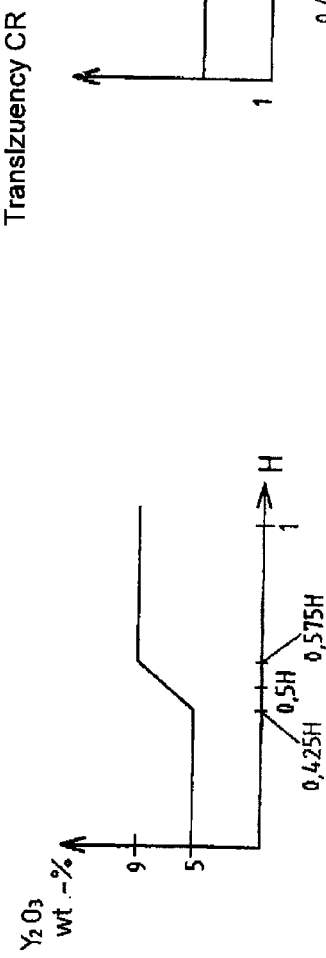

Substantial features of the invention's teaching will be illustrated again with the help of FIG. 10. FIG. 10 shows the blank 133 with the layers 114 and 124 as well as the transition region 128.

FIG. 10b illustrates that the content proportion of the stabilizing agent in the form of yttrium oxide in the first layer 114 is approximately 5% by weight and is approximately 9% by weight in the second layer 124, and that because of the invention's embodiment of the intermediate layer 128, the yttrium oxide content increases continuously. The numbers 0.425 H and 0.575 H emphasize that the element 116 that is shown in FIGS. 8 and 9 dips into the first layer 114 in a way so that valleys are formed, which are situated—relative to the total height H of the layers 114, 124—in a region of 0.075 H below the surface 118 and the elevations or mountains are situated in a region of 0.075 above the surface 118, whereby—as mentioned above—the distance between the peaks 120 and troughs 122 of the serrated structure of the element 116 is 0.15 H.

Measurements pursuant to DIN-ISO 6872 that were carried out onr the fully sintered layers 114 and 124 have shown that the flexural strength $\sigma_B$ in the layer 114, in which more than 80% of the zirconium dioxide is present in the tetragonal crystalline phase, is approximately 1000 MPa. In contrast, the flexural strength of the layer 124, in which 30-49% are present in the cubic crystalline phase, is approximately 660 MPa.

FIG. 10d illustrates the change in translucency across the height of the layers 114, 124.

Figure 12:
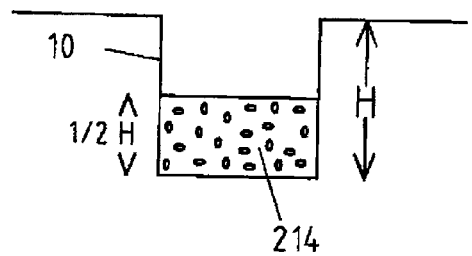
Figure 12:
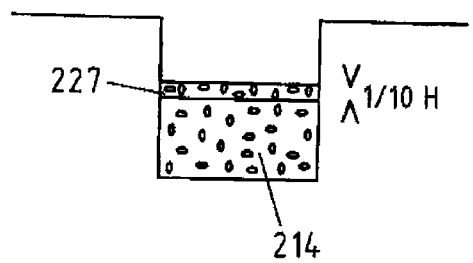
Figure 12:
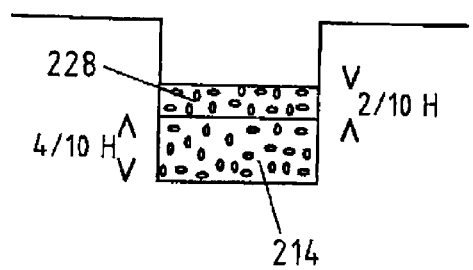
Figure 12:
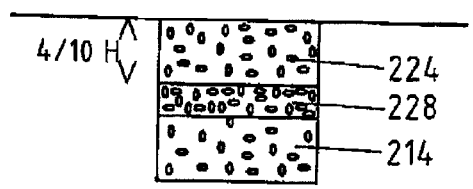

FIG. 12 will be used to explain an alternative method, which follows the invention's teachings to manufacture a blank or a dental restoration that offers a mostly continuous transition with respect to translucency and strength between a first layer and a second layer, or in the case of a restoration, between the dentine region and the incisal region.

In accordance with FIG. 12a, one at first introduces a first ceramic material, which should correspond to that of the layer 114 of FIG. 8 into a mold 110. The corresponding layer in FIG. 12a is identified with the label 214. The height of this layer may be half of the height of all the layers that are introduced into the mold 110. Onto the layer 214, one subsequently fills a layer 227 with a height that in the embodiment example is ⅒ of the total height of the layers. The material of the layer 227 can correspond to that of the second layer 124 of FIG. 8. This is followed by a mixing of the layer 227 with a surface region of the layer 214 throughout a depth that corresponds to the thickness of the layer 227. This creates an intermediate layer 228, which possesses a thickness of 2/10 of the overall height of the layers. Onto the intermediate layer 228, one subsequently applies a further layer 224, which corresponds to the second layer 124 of FIG. 8. The height of the layer 224 in the embodiment example consequently will be 4/10 of the total height H. Subsequently, in accordance with the embodiment example of FIG. 8, the layers 224, 228, 214 are pressed as a whole, which is followed by the process steps pre-sintering, machining, and sintering to final density, as was explained above. Of course it is also possible to carry out the machining after the sintering to final density.

The invention claimed is:

1. A method for manufacturing a colored blank comprising zirconium dioxide that is intended for the production of a dental restoration, the method comprising the steps of:
   introducing into a mold a layer of a first ceramic material, which includes at least one coloring element, with zirconium dioxide as the main constitute to form a first mixture, wherein a first open cavity is formed in the layer;
   introducing at least into the first open cavity a second ceramic material define a second layer, which includes a second mixture with a composition that is different from that of the first mixture;
   pressing the first mixture and the second mixture, and subsequently subject the pressed first and second mixtures to at least one thermal treatment,
   wherein the at least one coloring element in the raw materials in powder form is selected from the group consisting of terbium, erbium, cobalt, one element that generates a fluorescent effect in the dental restoration, and mixtures thereof,
   wherein iron, apart from natural impurities, is not present.

2. The method of claim 1, wherein bismuth is used as the element that generates the fluorescent effect.

3. The method of claim 1, wherein disregarding naturally occurring impurities, the raw materials include at least one of the following:
   a first raw material in powder form that includes bismuth as the element that generates the fluorescent effect;
   a second raw material in powder form that includes exclusively terbium, or terbium and praseodymium;
   a third raw material in powder form that includes exclusively erbium;
   a fourth raw material in powder form that includes exclusively cobalt, or cobalt and manganese, and/or cerium; and
   combination thereof.

4. The method of claim 1, wherein one of the raw materials in powder form is free of coloring elements, apart from natural impurities.

5. The method of claim 1, wherein raw materials in powder form includes yttrium-stabilized zirconium dioxide of the following composition:

$HfO_2 < 3.0\%$ by wt;

$Al_2O_3 < 0.3\%$ by wt;

Unavoidable impurities due to technical limitations $\leq 0.2\%$ by wt;

$Y_2O_3$ 4.5 to 9.5% by wt;

$ZrO_2 = 100\% - (Y_2O_3 + Al_2O_3 + HfO_2 + \text{unavoidable impurities})$ % by wt.

6. The method of claim 1, wherein after introduction of the second ceramic material, a second open cavity is created in the mold.

7. The method of claim 6, wherein into the second open cavity is filled a third ceramic material, which possesses a composition that is different from those of the first and/or second ceramic material.

8. The method of claim 1, wherein in the layer formed of the first ceramic material are formed several first open cavities and into these is filled the second ceramic material.

9. The method of claim 8, wherein at least some of the several open first cavities possess differing inside geometries.

10. The method of claim 1, wherein after sintering to full density, the second ceramic material possesses a thermal expansion coefficient that is 0.2 to 0.8 μm/m*K greater than that of the first ceramic material.

11. The method of claim 1, wherein the interior geometry of the first open cavity is geometrically matched to the shape of a dental jaw region that is to be provided with a restoration or to that of an abutment originating from a jaw region.

12. The method of claim 1, wherein when working the dental restoration out of the blank, a dentine region of the dental restoration is at least partially composed of the second ceramic material and an incisal region of the first ceramic material.

13. The method of claim 1, wherein the yttrium oxide content in the first ceramic material is 7.0% by weight to 9.5% by weight; and/or the yttrium content in the second and/or third ceramic material is 4.5% by weight to 7.0% by weight, whereby the yttrium oxide content in the first ceramic material is higher than that of the second or third material.

14. The method of claim 1, wherein in the first ceramic material or the second ceramic material, the quotient of the tetragonal crystal phase and the cubic crystal phase of the zirconium dioxide after pre-sintering is ≥1.

15. A method for the manufacture of a blank of a ceramic material, whereby at least two layers are introduced by filling into a mold ceramic material, which includes mixtures that were created in accordance with claim 1 and possess different compositions, and that after introduction of the layers, these are pressed and subsequently sintered, after introduction of a first layer comprising of a first mixture, the surface of this layer is structured in such a way that the surface of the first layer, viewed along the surface, possesses regions of different heights, and subsequently a second layer comprising of a mixture with a composition different from that of the first mixture is filled into the mold, or in that after introduction of the first layer, a further layer is filled on top of it into the mold, which includes of a mixture that is different from that of the first layer, in that the material of the first layer is intermixed with the material of the further layers to form an intermediate layer, and that subsequently the second layer is filled into the mold.

16. The method of claim 15, wherein the surface of the first layer is being structured in a way so that depressions and elevations are created whereby the latter confine the former.

17. The method of claim 15, wherein in a top view of the surface the created structure has an annular pattern, which comprises the depressions and the elevations bordering them.

18. The method of claim 1, wherein a structure is created by an element, which moves-relative to the first layer, and which structures a surface region of the first layer with a segment that is embodied with a wave-like, comb-like or serrated shape.

19. The method of claim 18, wherein the structure is created by a pressure element that acts along a direction perpendicular to the surface region of the first layer.

20. The method of claim 19, wherein the pressure element imprints into the surface region of the first layer elevations that extend concentrically or in parallel, and depressions extending in between the elevations.

21. The method of claim 15, wherein the structure is formed in such a way that the volume of the elevations is equal or approximately equal to the volume of the depressions.

22. The method of claim 15, wherein the material of the mixture of the additional layer is intermixed with the material of the mixture of the first layer downward from the free surface of the additional layer along a height that corresponds to twice or approximately twice the height of the additional layer.

23. The method of claim 22, wherein the mixture used for the additional layer is identical to that of the second layer.

24. The method of claim 1, wherein that contacting regions of the first layer and the second layer are mixed over a height that corresponds to ⅕ H to ¼ H, where H is the total height H of the first and second layer.

25. The method of claim 1, wherein that the first layer in an unstructured state possesses a height that corresponds to half or approximately half the height of the total height H of the first and second layer.

26. The method of claim 1, wherein the first and second ceramic mixtures used for the first layer and the second layer are such that the quotient of the tetragonal crystal phase to the cubic crystal phase of the zirconium dioxide in both the first layer and the second layer will be ≥1 after pre-sintering.

27. A pre-sintered or fully sintered blank that is manufactured in accordance with claim 1.

28. A pre-sintered or fully sintered blank to be used in the manufacture of a dental restoration, comprising a ceramic material that includes zirconium dioxide, and possesses regions of different compositions, whereby a first region includes a first ceramic material and at least a second region includes a second ceramic material of a different composition, and the regions adjoin each other, whereby in particular the first ceramic material and/or the second ceramic material include of a mixture according to claim 1, wherein the second region extends within the first region and possesses an outside geometry that narrows as the distance from a base region or base surface increases.

29. The blank of claim 28, wherein the base region extends in the area of an outer surface of the first region, and merges flush with the outer surface.

30. The blank of claim 28, wherein that the second region has a cavity that originates from its base region.

31. The blank of claim 28, wherein the second region possesses a cone-like exterior geometry.

32. The blank of claim 28, wherein within the second region extends a third region, which includes of a third ceramic material with a composition that is different from that of the first and/or second ceramic material.

33. The blank of claim 28, wherein a first region includes a plurality of layers, the plurality of layers each differing by composition.

34. The blank of claim 28, wherein at least a few of the plurality of layers have differing exterior geometries.

35. The blank of claim 28, wherein the blank includes zirconium dioxide doped with yttrium oxide.

36. The blank of claim 28, wherein the yttrium oxide content in the second ceramic material or the third ceramic material is between 4.5% by weight and 7.0% by weight, while the yttrium oxide content is between 7.0% by weight and 9.5% by weight in the first ceramic material, whereby the yttrium oxide content in the first ceramic material is greater than in the second ceramic material.

37. The blank of claim 28, wherein the second ceramic material is colored differently from the first ceramic material.

38. The blank of claim 28, wherein the amount of the element generating the fluorescent effect in the first ceramic material is different from that in the second ceramic material.

39. The blank of claim 28, wherein after sintering to full density, the dental restoration produced from the blank possesses a higher strength on a dentine side than on an incisal side and/or a higher translucency on the incisal side than on the dentine side and/or in the dentine region a higher content of the element generating the fluorescence effect than in the incisal region.

40. The blank of claim 28, wherein a thermal expansion coefficient of the first region is 0.2 μm/m*K to 0.8 μm/m*K lower than a thermal expansion coefficient of the second and/or third region.

41. The blank of claim 28, wherein the blank comprises at least three layers, one of which is a middle layer, which extends over at least ⅒ H to ⅕ H of the total height H of the blank, and which includes a material of the first layer and the second layer.

42. The blank of claim 41, wherein in the middle layer the fraction of the material of the first layer decreases along the direction from the first layer towards the second layer in a continuous or largely continuous manner.

43. The blank of claim 41, wherein the yttrium oxide content in the middle layer increases from the first layer towards the second layer in a continuous or largely continuous manner.

44. The blank of claim 41, wherein the first layer is colored differently than the second layer and/or includes different amounts of the element generating the fluorescent effect.

45. The blank of claim 41, wherein after the sintering to completeness of the blank, the dental restoration produced from the former exhibits, viewed along the tooth axis, a higher rigidity on the root side than on the incisal side and/or exhibits a higher translucency on the incisal side than on the root side.

46. A dental restoration, manufactured in accordance with claim 1, wherein the dental restoration is embodied monolithically and includes at least of a first layer, which includes of a first ceramic material and extends on the incisal side, and a second layer, which includes of a second ceramic material and extends on the dentine side, whereby the first layer possesses a higher translucency and/or lower rigidity and/or a lower degree of fluorescence than the second layer.

47. The dental restoration of claim 46, wherein a thermal expansion coefficient of the first layer is 0.2 μm/m*K to 0.8 μm/m*K lower than a thermal expansion coefficient of the second layer.

48. A dental restoration, produced from a blank of claim 28, wherein the dental restoration, viewed along the axial direction of the tooth, includes of at least a first layer extending on the root side, a second layer extending on the incisal side, and, extending in between these, a middle layer or intermediate layer, in which the strength decreases from the first layer towards the second layer in a continuous or largely continuous manner and/or in which the translucency increases continuously or largely continuously and/or in which the fluorescence characteristic decreases.

* * * * *